United States Patent [19]

Cosman

[11] Patent Number: 5,158,563
[45] Date of Patent: Oct. 27, 1992

[54] SINGLE-OPERATOR HEMORRHOID LIGATOR

[76] Inventor: Bard C. Cosman, 439 College Ave., Palo Alto, Calif. 94306-1525

[21] Appl. No.: 719,020

[22] Filed: Jun. 21, 1991

[51] Int. Cl.$^5$ .............................................. A61B 17/00
[52] U.S. Cl. ...................................... 606/140; 128/4; 128/5; 128/6
[58] Field of Search ................. 606/140, 144; 128/4-6

[56] References Cited

U.S. PATENT DOCUMENTS

| | | | |
|---|---|---|---|
| 3,382,873 | 7/1968 | Banich et al. | 128/326 |
| 3,760,810 | 10/1973 | Van Hoorn | 128/326 |
| 3,985,138 | 10/1976 | Jarvik | 606/144 |
| 4,257,419 | 1/1981 | Göltner et al. | 128/303 A |
| 4,374,523 | 2/1983 | Yoon | 606/140 |
| 4,794,927 | 6/1989 | Yoon | 128/326 |
| 4,869,268 | 9/1989 | Yoon | 606/158 |
| 5,020,514 | 6/1991 | Heckele | 128/4 |
| 5,026,379 | 6/1991 | Yoon | 606/141 |

OTHER PUBLICATIONS

Barron J: Office ligation treatment of hemorrhoids. *Diseases of the Colon and Rectum* 1963; 6:109–113. See p. 110.
Thomson H.: The one-man bander: a new instrument for elastic ligation of piles. *Lancet* 1980; 2(8202):1006–1007. See p. 1006.
Schofield P. F., Cunliffe W. J., Hulton N.: Elastic band ligation of haemorrhoids: a new applicator. *British Journal of Surgery* 1984; 71(3):212.
Barron J.: Office ligation of internal hemorrhoids. *American Journal of Surgery* 1963; 105:563–570. See pp. 563–564.
McGivney J.: Ligation treatment of internal hemorrhoids. *Texas Medicine* 1967; 63(5):56–59. See p. 57.
Rudd W. W. H.: Ligation of hemorrhoids as an office procedure. *Canadian Medical Association Journal* 1973; 108:56–59. See p. 57.
Keighley D. G.: Hemorrhoidal diseases and office ligation of hemorrhoids. *American Journal of Proctology, Gastroenterology & Colon & Rectal Surgery* 1979; 30(3):34–36. See p. 35.
Lamm H.: A simple new hemorrhoid ligator. *Diseases of the Colon and Rectum* 1973; 16:547–549. See pp. 547–548.
Orlay G.: Office treatment of haemorrhoids. *Medical Journal of Australia* 1979; 2(8):420.

*Primary Examiner*—Stephen C. Pellegrino
*Assistant Examiner*—Gary Jackson

[57] ABSTRACT

A surgical instrument for elastic ring ligation of hemorrhoids and similar body tissues by a single operator, comprising, in combination, a forceps (46) slidably disposed on ligator shaft (60) of a ligator (62) by means of a sliding fitting (58), an endoscope (20) with a track (32) fixedly attached to its inner wall, an obturator (34) receivable within the endoscope to facilitate the insertion of the endoscope into a body orifice, and a loading mandrel (78) allowing a contractible elastic ring (76) to be mounted on the ligator. The track conforms to the sliding fitting with friction sufficient to retain the forceps and ligator in place at any point along the track, but allowing the surgeon to push the sliding fitting along the track without excessive force.

16 Claims, 7 Drawing Sheets

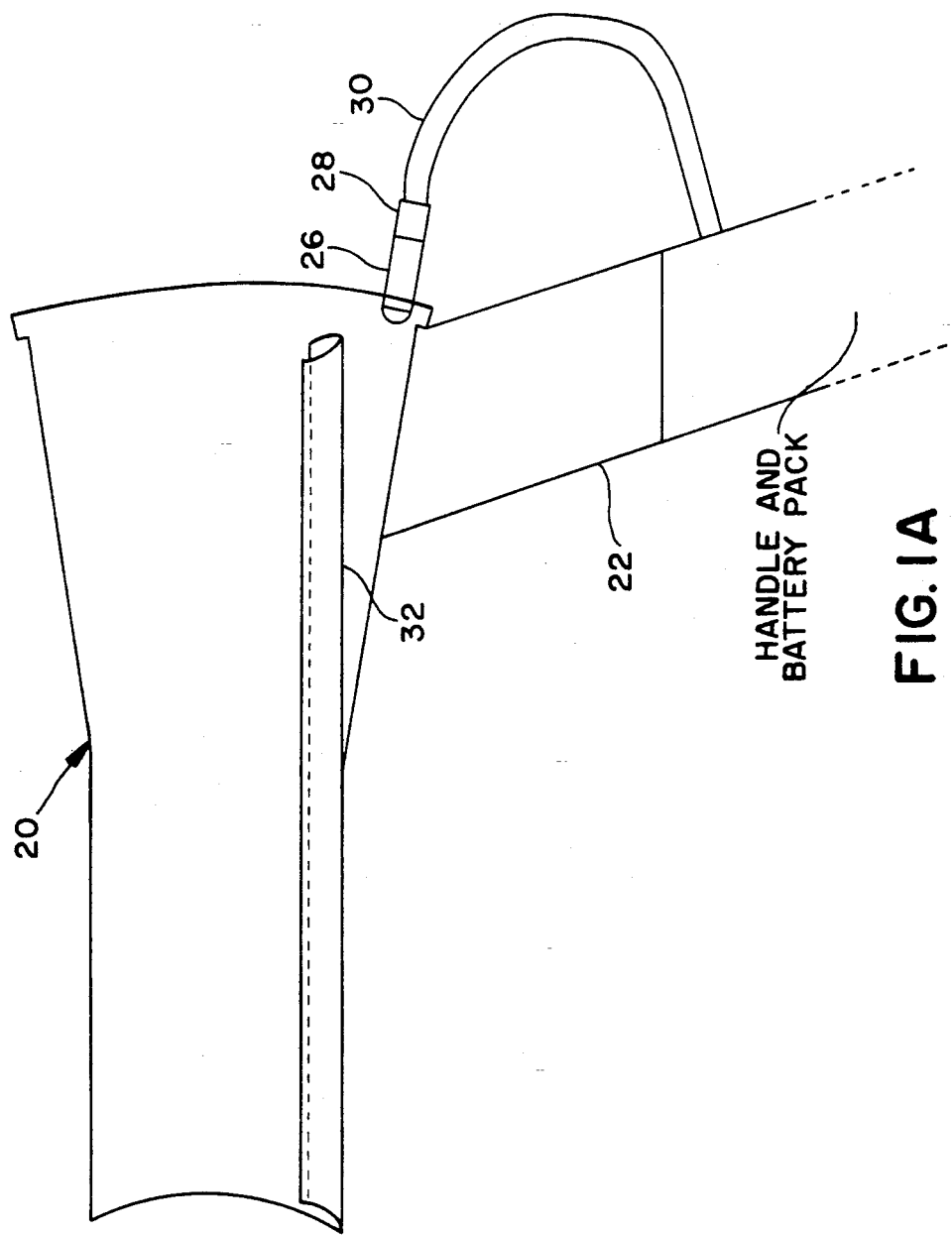

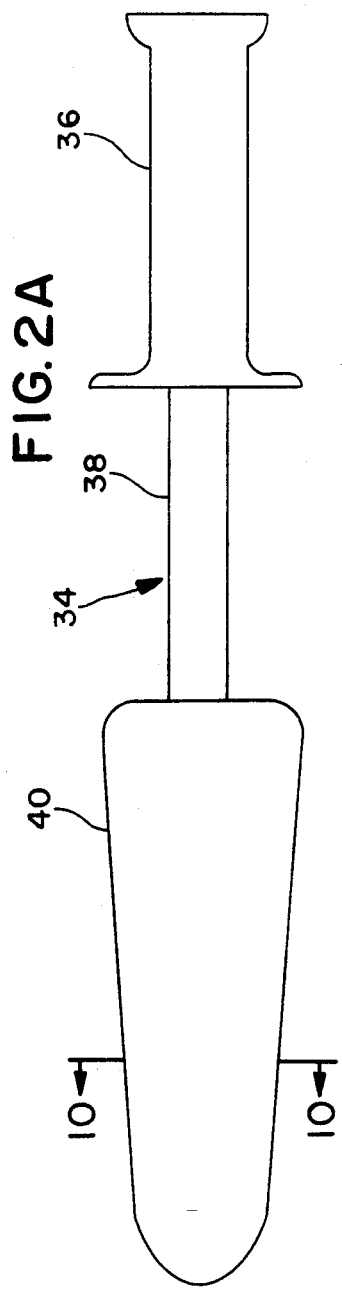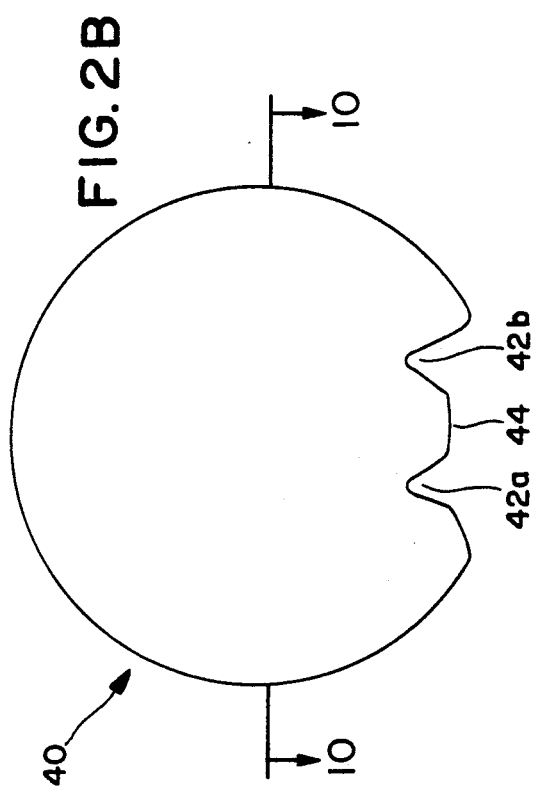

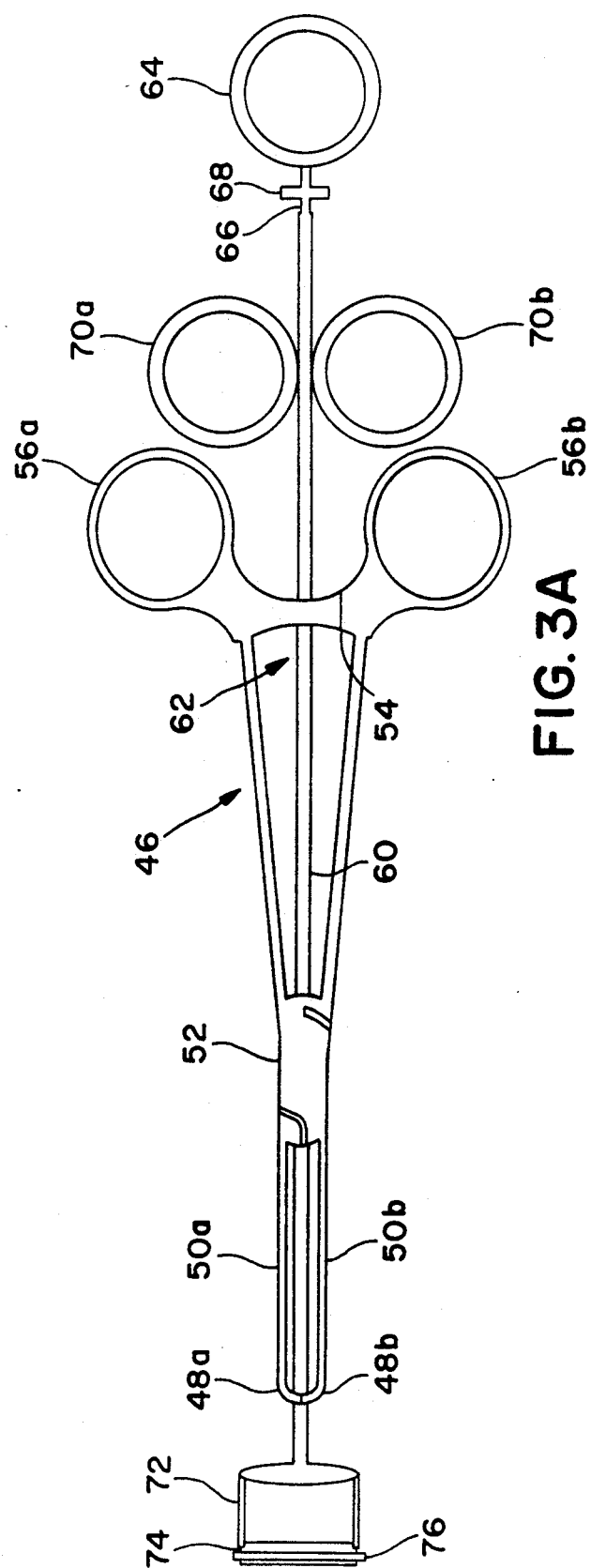

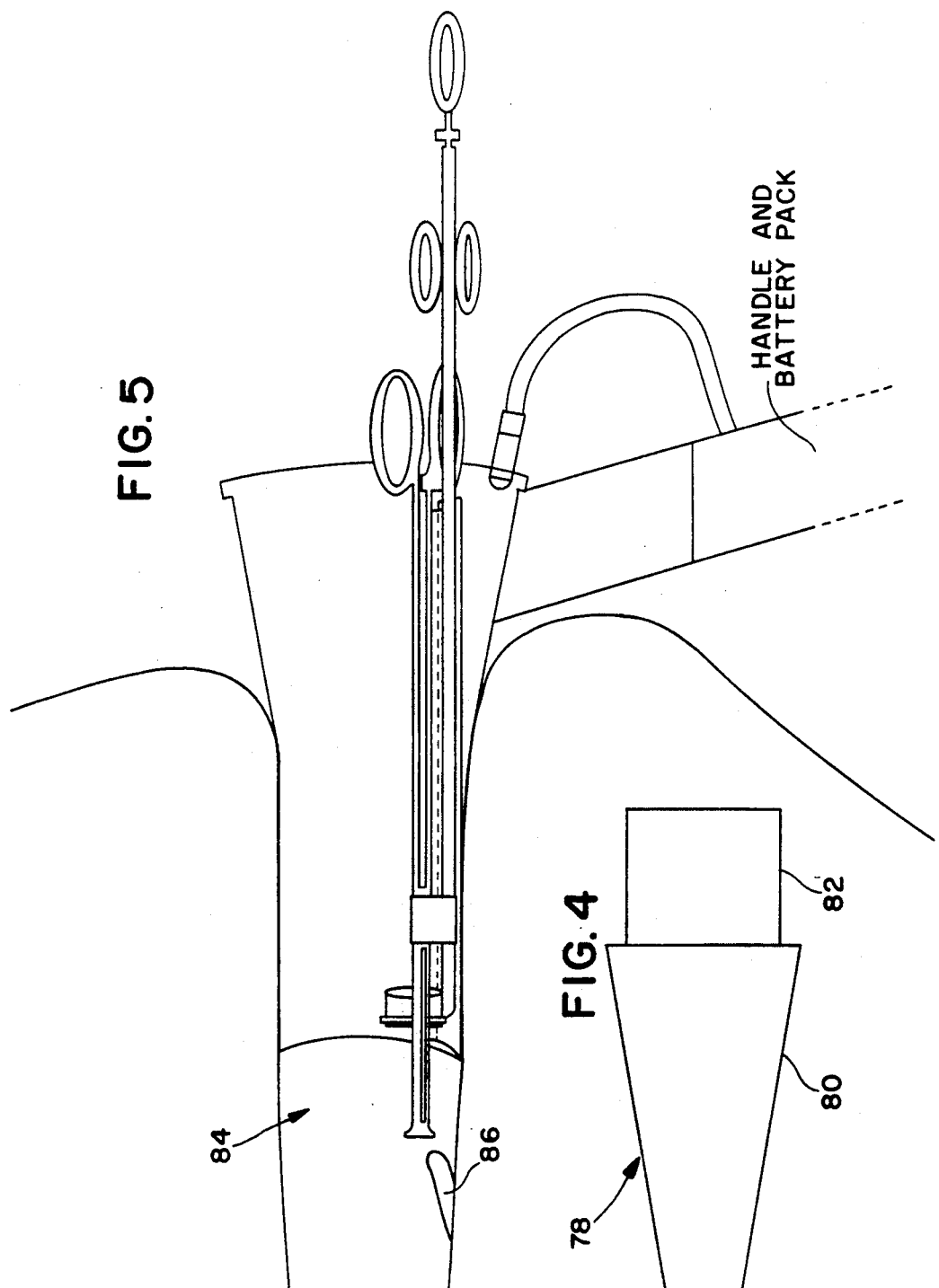

SINGLE-OPERATOR HEMORRHOID LIGATOR

FIELD OF INVENTION

This invention relates to an improved tissue ligating device, specifically to a single-operator device for treating hemorrhoids.

BACKGROUND AND DESCRIPTION OF PRIOR ART

Hemorrhoids and similar lesions (internal hemorrhoids, external hemorrhoids, perianal skin tags) are a frequent source or morbidity in the general population and in specific high-risk groups, such as those with spinal cord injuries. Surgical operation was long the mainstay of hemorrhoid treatment, but it has been largely replaced by a number of non-operative techniques, one of which is elastic ring ligation.

In this type of procedure, a tight elastic ring is placed around the base of the hemorrhoid, causing loss of blood supply and tissue death. The term "elastic" is used to indicate the propensity of an object for recovering its original size and shape after deformation by forces such as stretching. Elastic ring ligation may be accompanied by injection of medication for chemical destruction of the hemorrhoid. Elastic ring ligation is usually done without anesthesia or hospital admission, reducing costs and making it a procedure of choice both in industrialized and developing countries.

As generally practiced, elastic ring ligation requires three hand-held instruments: an endoscope (anoscope or anal speculum), a forceps, and a ligator. The endoscope has within it a removable, handled mandrel called an obturator, which facilitates the insertion of the endoscope into the orifice. Typically, the surgeon first introduces the endoscope (with the obturator in place) into the patient's anus to visualize the target lesion. The obturator is then withdrawn, allowing the surgeon to visualize the patient's hemorrhoids. As an assistant holds the endoscope in place, the surgeon grasps the hemorrhoid with the forceps and draws it through the barrel of the ligator, onto which a contractible elastic ring has previously been stretched. The elastic ring is displaced off the barrel of the ligator onto the base of the lesion. A problem with the procedure as typically practiced is that it requires at least three hands to perform, necessitating the presence of an assistant Prior art devices address this problem in two major ways: either two of the three instruments are combined or suction is used to substitute for forceps. In the former category, prior art includes a combination of forceps and ligator (Blaisdell's device, depicted in *Diseases of the Colon and Rectum* 6:110, 1963) and combinations of endoscope and ligator (U.S. Pat. No. 3,760,810 to Van Hoorn, Sept. 25, 1973, and Thomson's device, depicted in *Lancet* 2:1006, 1980). In the latter category, suction ligators include a described embodiment of Van Hoorn's device (cited above), the preferred embodiment in U.S. Pat. No. 4,257,419 to Göltner et al. (Mar. 24, 1981), and the Pyser device, depicted in *British Journal of Surgery* 71:212, 1984.

Suction ligators are only useful where controllable suction is available, making their use impractical in many offices, clinics, and hospitals both in industrialized and developing countries. In addition, the size of the lesion to be ligated is strictly limited by the depth of the suction vessel, a serious limitation for the aforementioned Göltner and Pyser devices.

Blaisdell's aforementioned combination of forceps and ligator has the disadvantage that the forceps and ligator are not self-retaining within the endoscope, forcing the surgeon to manage both forceps and ligator elements simultaneously with one hand, which is not practical. An assistant is still required to hold the endoscope while the surgeon operates the forceps and ligator with two hands.

Van Hoorn's and Thomson's devices, each of which combines endoscope and ligator in a single instrument and leaves the forceps to be manipulated by the surgeon's free hand, are usable by a single operator, but they stop short of uniting all three instruments in an efficient combination. In addition, they have the disadvantage of requiring the use of two hands at all times during the procedure.

There are many variations in design of the three instruments (ligator, forceps, and endoscope) used in elastic ring ligation of hemorrhoids. A large number of ligator design variations exists. Among ligators, variations in the grip for the actuation mechanism include pistol-grip (Barron type, depicted in *American Journal of Surgery* 105:563, 1963), speculum-grip (McGivney type, depicted in *Texas Medicine* 63(5):57, 1967), finger-ring grip (Rudd Clinic type, depicted in *Canadian Medical Association Journal* 108:57, 1973), scissors-grip (Keighley type, depicted in *American Journal of Proctology, Gastroenterology, & Colon & Rectal Surgery* 30(3):35, 1979), etc.

Variations in the mechanism for pushing the contractible elastic ring off the ligator's barrel include the use of a dual barrel (U.S. Pat. No. 3,382,873 to Banich et al., May 14, 1968, or Barron or McGivney type, cited above), the use of a pullstring (Lamm type, depicted in *Diseases of the Colon and Rectum* 16:547, 1973), the use of a pushrod (Rudd Clinic type, cited above), etc. For elastic ring ligation accompanied by injection of medication for chemical destruction of the hemorrhoid, a needle and injection port can be affixed to the ligator (Orlay type, depicted in *Medical Journal of Australia* 2:420, 1979).

Numerous varieties of forceps can be used to grasp hemorrhoids for elastic ring ligation; the most practical are toothed, including Allis type and hemorrhoid grasping forceps (depicted in *American Journal of Surgery* 105:564, 1963). Endoscopes used for hemorrhoid treatment are typically either solid-sided or slotted. For the purposes of this invention, all the above variations in ligator, forceps, and endoscope are considered equivalent, as this invention relates to a new device which combines the three instruments.

Likewise, several variations of elastic ring design exist. U.S. Pat. No. 4,794,927 to Yoon, Jan. 3, 1989, describes a family of elastic rings incorporating different types of interconnecting elements. These have, to varying degrees, the advantage of adhering more securely to the hemorrhoid (or other ligated structure) than the smooth elastic ring used conventionally. For the purposes of this invention, these variations in the design of elastic ring are considered equivalent, as this invention relates to a new device which combines ligator, forceps, and endoscope.

OBJECTS AND ADVANTAGES

Accordingly, several objects and advantages of the present invention are:

(a) to combine the three instruments used for elastic ring ligation of hemorrhoids (ligator, forceps, and endoscope) so as to allow the procedure to be performed efficiently and conveniently by a single operator, eliminating the necessity for an assistant;

(b) to allow single-operator elastic ring ligation of hemorrhoids without the need for cumbersome supplemental equipment such as suction apparatus;

(c) to make the forceps and ligator self-retaining within the endoscope, so that the surgeon might have one hand free at any point during the procedure, with the elements of the device staying in place until that hand could be used to complete the procedure.

Other objects and advantages will become apparent from a consideration of the ensuing description and drawings.

DRAWING FIGURES

In the drawings, closely related figures have the same number but different alphabetic suffixes.

FIGS. 1A and 1B are cutaway side and end views of the endoscope element of the invention.

FIGS. 2A and 2B are side and cross-sectional views of the obturator element of the invention.

FIGS. 3A and 3B are top and oblique side views of the forceps and ligator elements of the invention.

FIG. 4 is a side view of a loading mandrel usable for stretching a contractible elastic ring over the barrel of the ligator of the invention.

FIG. 5 is a cutaway side view of the assembled device in operation, in position to grasp a hemorrhoid within the anal canal.

Figure 1B:
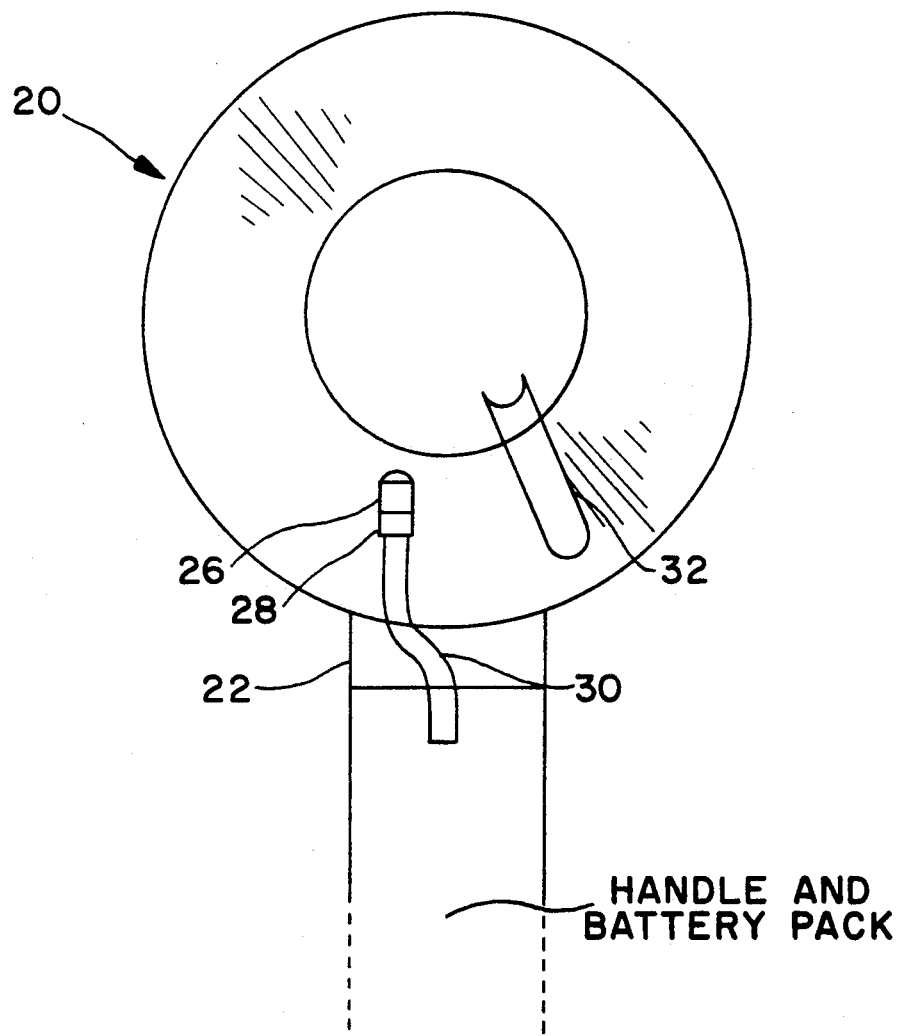

REFERENCE NUMERALS IN DRAWINGS 20 endoscope
22 endoscope support
26 bulb
28 bulb housing
30 light support
32 track
34 obturator
36 obturator handle
38 obturator shaft
40 head
42a and 42b notches
44 ridge
46 forceps
48a and 48b jaws
50a and 50b arms
52 hinge
54 locking mechanism
56a and 56b forceps finger-rings
58 sliding fitting
60 ligator shaft
62 ligator
64 pushrod handle
66 pushrod
68 adjusting collar
70a and 70b ligator finger-rings
72 barrel
74 shelf
76 elastic ring
78 loading mandrel
80 conical segment
82 cylindrical segment
84 anal canal
86 hemorrhoid

DESCRIPTION—FIGS. 1 TO 4

The elements of the invention (endoscope 20, obturator 34, forceps 46, ligator 62, and loading mandrel 78) are preferably made of stainless steel or a biologically inert plastic. Some or all elements can be disposable. Elastic ring 76 is preferably made of latex rubber, silicone rubber, or other biologically compatible, contractible, elastic polymer.

FIGS. 1A and 1B show cutaway side and end views of the endoscope element of the invention. A tapered endoscope 20 (the one depicted is modified from an anoscope available from Welch Allyn, Inc., Skaneateles Falls, NY) is fixedly attached to an endoscope support 22, which is connected to a handle and a source of electrical energy such as a battery pack or an electrical outlet (these conventional parts are indicated by the words "Handle and Battery Pack" in FIGS. 1A, 1B, 5, and 6). A bulb 26 is mounted within a bulb housing 28, which is attached to a light support 30. Light support 30 is fixedly attached to endoscope support 22. A track 32 of approximately U-shaped cross-section is fixedly attached to the inner surface of endoscope 20. Light support 30 and track 32 are positioned radially so that bulb 26 and light support 30 do not interfere with operation of the assembled device.

FIG. 2A shows a side view of the obturator element of the invention (the one depicted is modified from an obturator available from Welch Allyn, Inc., Skaneateles Falls, NY). An obturator 34 comprises a T-shaped obturator handle 36, which is fixedly attached to an obturator shaft 38, which in turn is fixedly attached to a head 40. Cross-section markings 10 refer to FIG. 2B.

FIG. 2B shows a cross-sectional view of the obturator element of the invention, corresponding to cross-section markings 10 in FIG. 2A. Head 40 has in its outer surface two notches 42a and 42b with a ridge 44 between them, of such dimensions as to engage track 32 loosely.

Figure 3B:
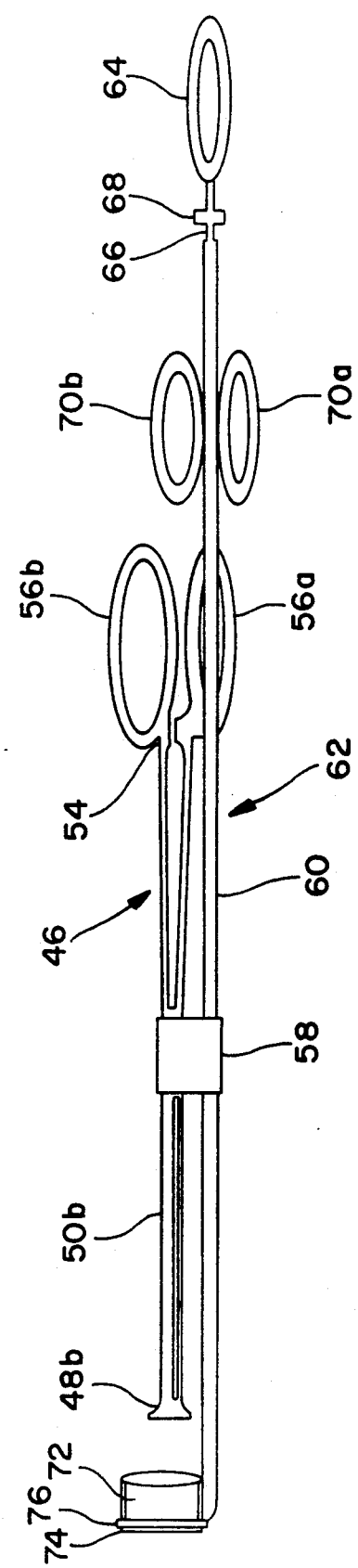

FIGS. 3A and 3B show top and oblique side views of the forceps and ligator elements of the invention. An Allis type forceps 46 (the one depicted is modified from a standard model available from many sources, including Pilling Co., Fort Washington, PA), having jaws 48a and 48b, two arms 50a and 50b, a hinge 52, a locking mechanism 54, and forceps finger-rings 56a and 56b, is fixedly attached to a sliding fitting 58 having a convex outer surface (shown in FIG. 3B), which is disposed slidably along ligator shaft 60 of a Rudd Clinic-type ligator 62 (the one depicted is available from Misdom-Frank & Sklar, West Chester, PA).

Ligator 62 has at one end a pushrod handle 64 having a threaded female end adjustably attached to the threaded male end of a pushrod 66. An adjusting collar 68 with a threaded inner surface also fits around the threaded male end of pushrod 66. Pushrod 66 is disposed slidably within ligator shaft 60, to which are attached ligator finger-rings 70a and 70b. On the opposite end of ligator 62 is an open cylindrical barrel 72, having a shelf 74 upon which a contractible elastic ring 76 can be mounted. Pushrod 66 ends in a hook-like member (shown in FIG. 3B) which can push elastic ring 76 off shelf 74.

FIG. 4 shows a side view of a loading mandrel 78 usable for stretching elastic ring 76 over shelf 74 of barrel 72 of ligator 62 of the invention. Loading mandrel 78 has a cylindrical segment 82 of such dimensions as to fit snugly within barrel 72 of ligator 62, and a conical segment 80 with its greatest diameter equal to that of shelf 74.

OPERATION—FIGS. 1 TO 6

The instrument according to the invention can be prepared for operation as follows: First, elastic ring 76 is placed over the tip of conical segment 80 of loading mandrel 78, of which cylindrical segment 82 is placed within barrel 72 of ligator 62. Elastic ring 76 is rolled up and over conical segment 80 of loading mandrel 78 and onto shelf 74, and loading mandrel 78 is put aside—ligator 62 is now loaded and ready for use, as in FIGS. 3A and 3B.

Holding forceps 46 by forceps finger-rings 56a and 56b, the surgeon advances it forward on ligator shaft 60 so that jaws 48a and 48b protrude through barrel 72. Forceps 46 and ligator 62 are now ready for use. Obturator 34 is placed within endoscope 20, making it ready for insertion.

The procedure for elastic ring ligation of a hemorrhoid using the instrument according to the invention is as follows: The surgeon introduces endoscope 20 (with obturator 34 in place) into the patient's anus. Obturator 34 is then withdrawn, leaving endoscope 20 in place for visualizing the patient's hemorrhoids. The surgeon then rotates endoscope 20 so that track 32 is directed towards the target lesion. The surgeon holds endoscope 20 in place by its handle (indicated by the words "Handle and Battery Pack") throughout the procedure.

Holding forceps 46 by forceps finger-rings 56a and 56b, the surgeon places sliding fitting 58 in track 32 and urges it distally until jaws 48a and 48b are adjacent to the target lesion. FIG. 5 shows a cutaway side view of this stage of the operation, with the device in a patient's anal canal 84 and a hemorrhoid 86 about to be ligated. Hemorrhoid 86 is then grasped with forceps 46, which is locked using locking mechanism 54 and drawn back sufficiently to expose the base of hemorrhoid 86. Forceps 46 then retains its position because of friction between sliding fitting 58 and track 32.

Figure 6:
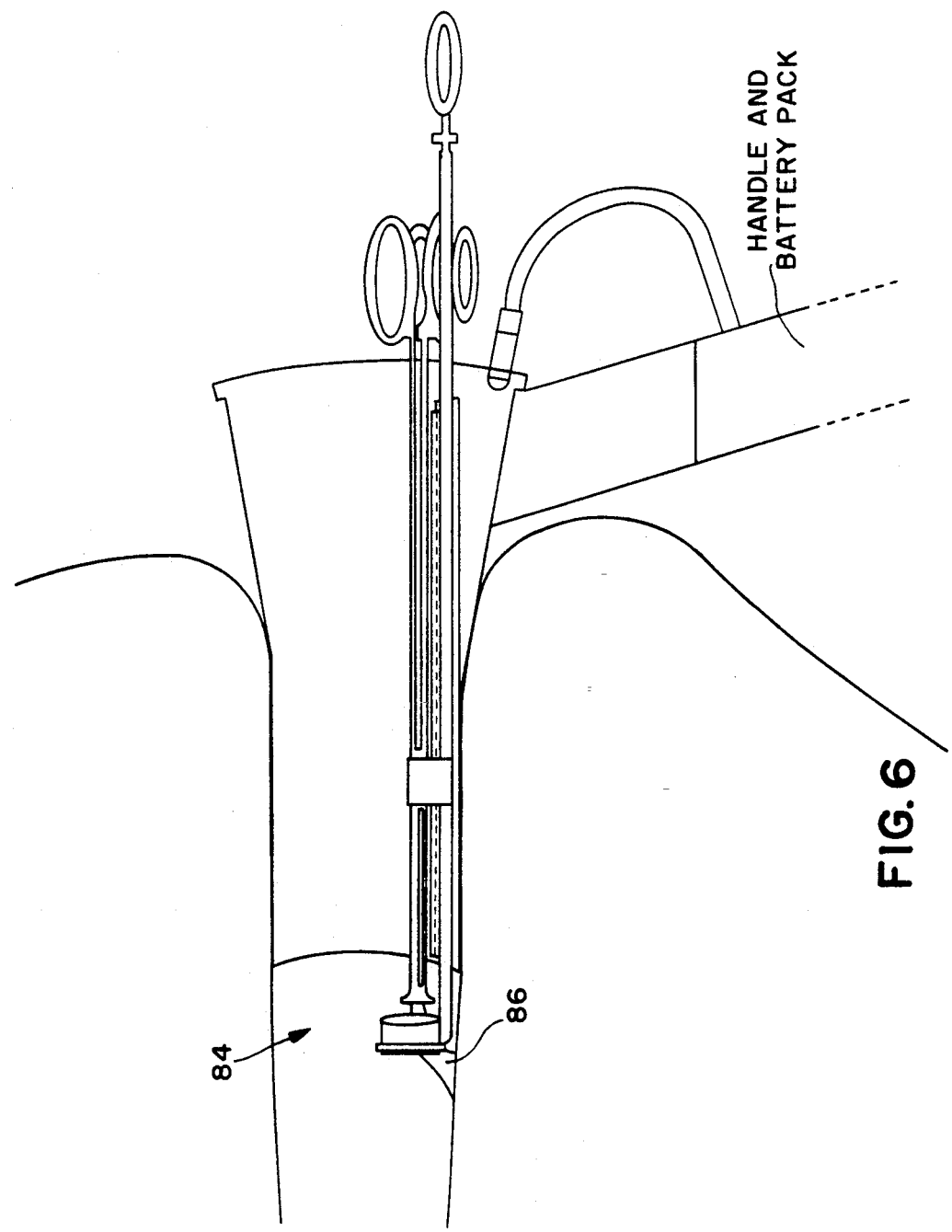
FIG. 6 is a cutaway side view of the assembled device in operation, in position to place a contractile elastic ring around the base of a hemorrhoid that has been grasped.

Holding ligator 62 by ligator finger-rings 70a and 70b, the surgeon then urges ligator 62 forward, sliding barrel 72 over closed jaws 48a and 48b and over hemorrhoid 86. FIG. 6 shows a cutaway side view of this stage of the operation. Elastic ring 76 is then displaced off shelf 74 by pushrod 66, actuated by pushrod handle 64. It will be seen that this procedure requires two hands to complete and confers an additional advantage in that the surgeon can stop at any point, leaving forceps 46 and ligator 62 in place, with one hand holding endoscope 20 in place.

Upon completion of the above procedure, locking mechanism 54 is disengaged, and all elements of the device are removed from the patient. If elastic ring ligation of another lesion is indicated, the instrument is again prepared for operation as above, and the procedure is repeated.

SUMMARY, RAMIFICATIONS, AND SCOPE

The instrument of the invention comprises a forceps attached to a ligator by a sliding fitting, and an endoscope with a track attached to or inset into its inner wall, which track conforms to the sliding fitting with friction sufficient to retain the forceps and ligator in place at any point along the track, but allowing the surgeon to push the fitting along the track without excessive force.

Accordingly, the reader will see that the instrument of the invention allows a single operator, working unassisted, to perform elastic ring ligation of hemorrhoids without the need for supplemental equipment such as suction apparatus. In addition, the ability of the forceps and ligator to self-retain within the endoscope allows the surgeon to have one hand free at any point during the procedure, with the elements of the device staying in place until that hand can be used to complete the procedure.

It will be apparent that the instrument of the invention can be useful for elastic ring ligation of hemorrhoids, but can be used for elastic ring ligation of other anatomical structures or lesions located within various orifices, whether in human patients or in animals.

Although the description above contains many specificities, these should not be construed as limiting the scope of the invention but as merely providing an illustration of a presently preferred embodiment of this invention. For example:

the grip for the actuation mechanism of the ligator can be of other types, such as pistol-grip (Barron type), speculum-grip (McGivney type), scissors-grip (Keighley type), etc.;

the ligator can bear a needle and injection port (Orlay type) for additional injection of medication;

the mechanism for pushing the contractible elastic ring off the barrel can be of other types, such as dual-barrel (Banich, Barron, or McGivney type), pullstring-actuated (Lamm type), etc.;

the barrel of the ligator can have a non-circular cross-section, such as elliptical, ovoid, etc.;

the junction between conical and cylindrical segments of the loading mandrel can have other conformations, such as with a bevelled or overhanging lip;

the contractible elastic ring can incorporate interconnecting elements of any type;

the forceps can be of other types, such as non-locking, scissor-grip, double-hinge, etc.;

the jaws of the forceps can be of other types, such as ridged, single-toothed, non-crushing, specialized for hemorrhoid grasping, etc.;

the endoscope can have other shapes, such as cylindrical, slotted, windowed, openable, etc.;

the endoscope can be of different lengths, such as a proctoscope, rigid sigmoidoscope, etc.;

the light source within the endoscope can be of other types, such as a fiberoptic cable, annular light guide, etc.;

the track within the endoscope can be an integral part of the wall of the endoscope;

the track and sliding fitting can be formed in any combination of two shapes that conform to each other with sufficient friction;

the track can be constructed in other ways, such as with friction increasing with forward position of the sliding fitting, with points along the track where the friction is increased; with variable friction controllable by the operator, etc.;

the obturator head can have any cutout or raised portion consistent with the shape of the track and the interior of the endoscope;

the obturator handle can have other shapes, such as straight, cruciform, constructed to include a finger-ring, etc.

Thus the scope of the invention should be determined by the appended claims and their legal equivalents, rather than by the examples given.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

I claim:

1. A surgical instrument for placing a contractible elastic ring about an anatomical structure within a body orifice, comprising in combination:
   (a) ligator means for holding said contractible elastic ring in a stretched condition and controllably releasing said contractible elastic ring, having at one end means for holding and releasing said contractible elastic ring and at the opposite end actuation means, with a shaft disposed between the two ends;
   (b) a loading mandrel for mounting said contractible elastic ring on said ligator means;
   (c) a forceps fixedly attached to a fitting slidably disposed around said shaft of said ligator means;
   (d) an endoscope having longitudinally disposed within it track means for allowing said fitting to slide with friction great enough to retain said forceps and said ligator means at any point along said track means, but small enough to be overcome by manual urging;
   (e) an obturator receivable within said endoscope to facilitate the insertion of said endoscope into a body orifice;
   whereby a single operator can perform elastic ring ligation of hemorrhoids conveniently and efficiently.

2. The surgical instrument of claim 1 wherein said forceps has a locking mechanism.

3. The surgical instrument of claim 1 wherein said endoscope is an anoscope.

4. The surgical instrument of claim 1 wherein said endoscope has within it a source of illumination.

5. The surgical instrument of claim 1 wherein said track means has a U-shaped cross-section.

6. The surgical instrument of claim 1 wherein any of its elements is composed of a biologically inert plastic material.

7. The surgical instrument of claim 1 wherein any of its elements is composed of stainless steel.

8. A surgical instrument for placing a contractible elastic ring about an anatomical structure within a body orifice, comprising in combination:
   (a) ligator means for holding said contractible elastic ring in a stretched condition and controllably releasing said contractible elastic ring, having at one end means for holding and releasing said contractible elastic ring and at the opposite end actuation means, with a shaft disposed between the two ends;
   (b) a forceps fixedly attached to a fitting slidably disposed around said shaft of said ligator means;
   (c) an endoscope having longitudinally disposed within it track means for allowing said fitting to slide with friction great enough to retain said forceps and said ligator means at any point along said track means, but small enough to be overcome by manual urging;
   whereby a single operator can perform elastic ring ligation of hemorrhoids conveniently and efficiently.

9. The surgical instrument of claim 8, further including a loading mandrel for mounting said contractible elastic ring on said ligator means.

10. The surgical instrument of claim 8, further including an obturator receivable within said endoscope to facilitate the insertion of said endoscope into a body orifice.

11. The surgical instrument of claim 8 wherein said forceps has a locking mechanism.

12. The surgical instrument of claim 8 wherein said endoscope is an anoscope.

13. The surgical instrument of claim 8 wherein said endoscope has within it a source of illumination.

14. The surgical instrument of claim 8 wherein said track means has a U-shaped cross-section.

15. The surgical instrument of claim 8 wherein any of its elements is composed of a biologically inert plastic material.

16. The surgical instrument of claim 8 wherein any of its elements is composed of stainless steel.

* * * * *